(12) United States Patent
Dennis et al.

(10) Patent No.: US 9,361,658 B2
(45) Date of Patent: Jun. 7, 2016

(54) SYSTEM AND METHOD FOR ENHANCED PROTECTION AND CONTROL OVER THE USE OF IDENTITY

(71) Applicants: Gary M. Dennis, Indian Springs, AL (US); Sharon D. Dennis, Indian Springs, AL (US)

(72) Inventors: Gary M. Dennis, Indian Springs, AL (US); Sharon D. Dennis, Indian Springs, AL (US)

(*) Notice: Subject to any disclaimer, the term of this patent is extended or adjusted under 35 U.S.C. 154(b) by 0 days.

(21) Appl. No.: 14/218,128

(22) Filed: Mar. 18, 2014

(65) Prior Publication Data

US 2014/0207681 A1    Jul. 24, 2014

Related U.S. Application Data

(60) Division of application No. 13/692,218, filed on Dec. 3, 2012, now Pat. No. 8,719,953, which is a division of application No. 12/805,337, filed on Jul. 26, 2010, now Pat. No. 8,353,027, which is a continuation of application No. 11/115,239, filed on Apr. 27, 2005, now Pat. No. 7,779,456.

(51) Int. Cl.

| | |
|---|---|
| G06Q 20/40 | (2012.01) |
| G06Q 50/26 | (2012.01) |
| G06F 21/62 | (2013.01) |
| G06Q 50/24 | (2012.01) |
| G07C 9/00 | (2006.01) |
| H04L 29/06 | (2006.01) |
| G06Q 20/10 | (2012.01) |

(52) U.S. Cl.
CPC .......... *G06Q 50/265* (2013.01); *G06F 21/6245* (2013.01); *G06Q 20/40* (2013.01); *G06Q 20/4014* (2013.01); *G06Q 50/24* (2013.01); *G07C 9/00087* (2013.01); *H04L 63/08* (2013.01); *H04L 63/104* (2013.01); *G06F 2221/2105* (2013.01); *G06F 2221/2137* (2013.01)

(58) Field of Classification Search
CPC . G06Q 20/023; G06Q 30/06; G06Q 30/0215; G06Q 20/4016; G06Q 30/0225
See application file for complete search history.

(56) References Cited

U.S. PATENT DOCUMENTS

| | | | | |
|---|---|---|---|---|
| 5,819,226 | A | * | 10/1998 | Gopinathan et al. ............ 705/44 |
| 5,884,289 | A | * | 3/1999 | Anderson et al. ............... 705/44 |
| 6,061,791 | A | | 5/2000 | Moreau |
| 6,094,643 | A | * | 7/2000 | Anderson et al. ............... 705/44 |
| 6,332,134 | B1 | | 12/2001 | Foster |
| 6,529,885 | B1 | | 3/2003 | Johnson |
| 6,711,685 | B1 | | 3/2004 | Schaal et al. |

(Continued)

FOREIGN PATENT DOCUMENTS

| | | |
|---|---|---|
| EP | 0038147 A1 | 10/1981 |
| WO | WO 0152518 A1 * | 7/2001 |

OTHER PUBLICATIONS

International Search Report and Written Opinion, International Application No. PCT/US6/12546, mailed Jul. 24, 2007.

*Primary Examiner* — Venkat Perungavoor
(74) *Attorney, Agent, or Firm* — Arent Fox LLP

(57) ABSTRACT

A method of protecting use of an entity's identity is provided. The method comprises setting a status of the identity to a first state, the first state defining a scope of permitted use of the identity, changing, in advance of an intended use of the identity, the status to a second state defining a scope of permitted use of the identity that is different from the first state, requesting use of the identity after the changing; and returning, after the requesting, the state back to the first state.

16 Claims, 6 Drawing Sheets

(56) References Cited

U.S. PATENT DOCUMENTS

| | | |
|---|---|---|
| 6,811,082 B2 | 11/2004 | Wong |
| 7,096,003 B2 * | 8/2006 | Joao et al. ............. 455/406 |
| 2001/0032192 A1 * | 10/2001 | Putta et al. ............. 705/76 |
| 2002/0004831 A1 | 1/2002 | Woodhill |
| 2002/0025797 A1 | 2/2002 | Joao et al. |
| 2002/0059430 A1 | 5/2002 | Orbke et al. |
| 2003/0028481 A1 | 2/2003 | Flitcroft et al. |
| 2003/0037233 A1 | 2/2003 | Pearson |
| 2003/0065626 A1 | 4/2003 | Allen |
| 2003/0070101 A1 | 4/2003 | Buscemi |
| 2003/0187759 A1 * | 10/2003 | Arthus et al. ............. 705/30 |
| 2003/0208439 A1 | 11/2003 | Rast |
| 2004/0004117 A1 | 1/2004 | Suzuki |
| 2004/0010472 A1 * | 1/2004 | Hilby et al. ............. 705/67 |
| 2004/0044905 A1 | 3/2004 | Heath et al. |
| 2004/0078324 A1 * | 4/2004 | Lonnberg et al. ............. 705/39 |
| 2004/0111329 A1 * | 6/2004 | Moore ............. 705/26 |
| 2004/0139025 A1 | 7/2004 | Coleman |
| 2004/0148256 A1 * | 7/2004 | Bramnick et al. ............. 705/40 |
| 2004/0168082 A1 | 8/2004 | Foster et al. |
| 2004/0215980 A1 | 10/2004 | Hamid |
| 2005/0044396 A1 | 2/2005 | Vogel et al. |
| 2005/0086541 A1 | 4/2005 | Rajaniemi |
| 2005/0137984 A1 | 6/2005 | Nguyen et al. |
| 2005/0149455 A1 * | 7/2005 | Bruesewitz et al. ............. 705/64 |
| 2005/0182712 A1 * | 8/2005 | Angell ............. 705/39 |
| 2005/0267827 A1 * | 12/2005 | Grant et al. ............. 705/35 |

\* cited by examiner

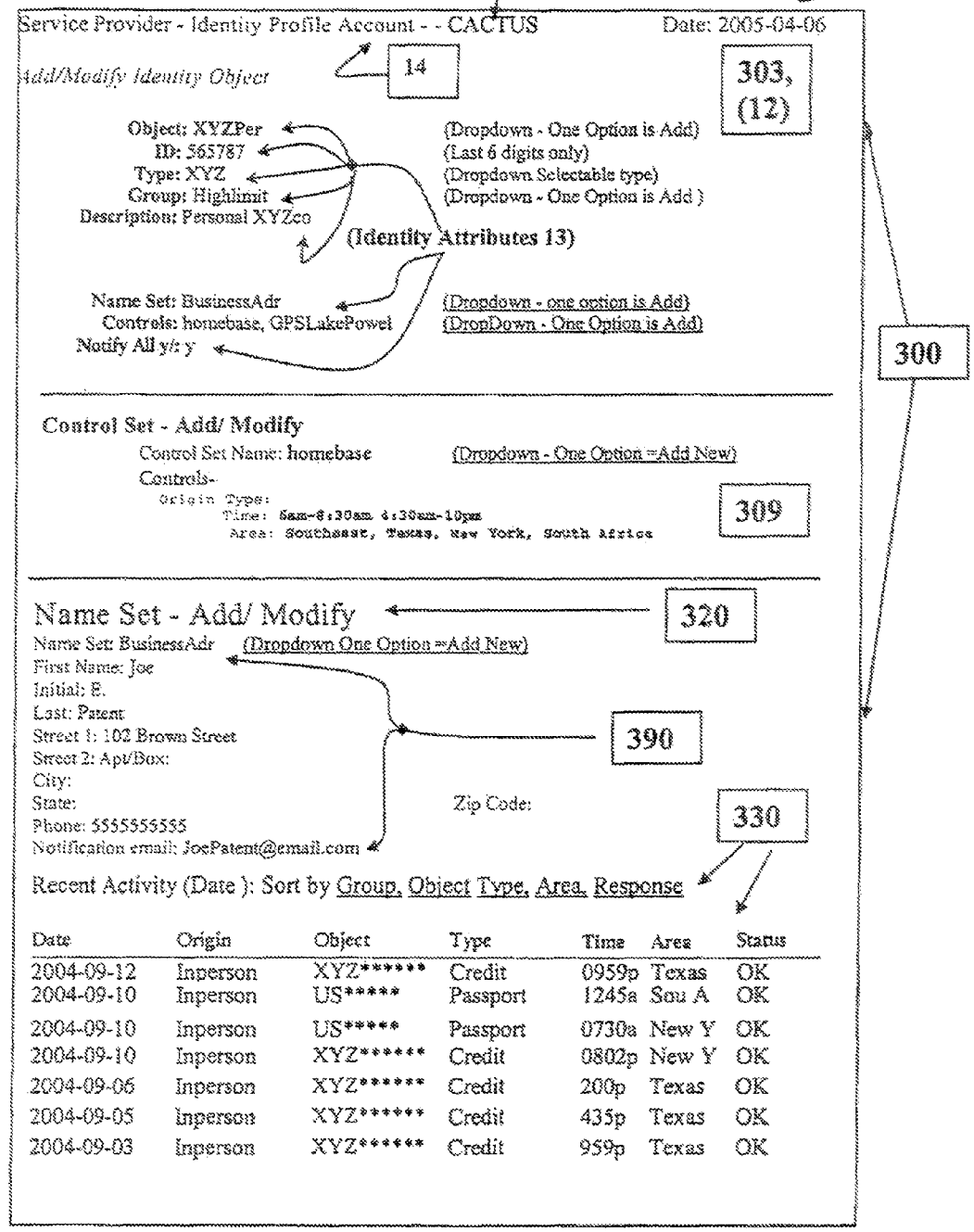

SYSTEM AND METHOD FOR ENHANCED PROTECTION AND CONTROL OVER THE USE OF IDENTITY

CROSS REFERENCE TO RELATED APPLICATIONS

This application is a Divisional of U.S. patent application Ser. No. 13/692,218 filed on Dec. 3, 2012, which is a Divisional of U.S. patent application Ser. No. 12/805,337 (now U.S. Pat. No. 8,353,027) filed on Jul. 26, 2010, which is a Continuation of U.S. patent application Ser. No. 11/115,239 (now U.S. Pat. No. 7,779,456) issued on Aug. 17, 2010 the disclosure of which is incorporated herein by reference in their entireties.

BACKGROUND OF THE INVENTION

1. Field of the Invention

The present invention relates to the protection of identity by controlling access to use of an identity. More specifically, the present invention provides protection of the identity of an entity by placing limitations or conditions on its use, and whereby the entity's use-enabling identification information is not fully needed to authorize a transaction.

2. Discussion of Background Information

Identity information can be, and has been, exploited so as to cause an identity owner and other ancillary parties emotional and financial harm. Examples of misuse of identity range from impersonation to financial fraud, such as a fraudulent loan application, fraudulent credit instrument use, check fraud, and other transactional frauds. Tens of billions of dollars are lost each year in the United States alone due to identity theft, with estimates rising as of the writing of this application. This does not account for the additional cost of law enforcement efforts to capture and bring perpetrators to justice.

With the increased technical and Internet literacy of our culture, identity theft is no longer limited to instances where financial gain is the sole motive. Indeed, it has now become necessary not only to protect our most precious identification information from use by an unscrupulous stranger, but there must also be in place a system that allows an identity owner to protect his identification information from use by a known party such as a disgruntled employee. With the ability and ease that identification information can be used to commit fraud against an identity owner as well as the resulting added burden on courts and law enforcement, there is a need for a system to protect the identity of an entity from misuse at a more fundamental level.

Traditional responses to this problem have been inadequate. The most common response involves monitoring the use of identity resources and notifying a consumer after detection of an unusual use of the identity. For example, a credit card company can detect unusual purchase activity and contact the account holder to determine whether the charges were authorized. While such monitoring mitigates against any continuing misuse of identity, responsive action is generally limited to apportion the burden of the harm between the victimized parties and seek prosecution of the offender. Such methods are thus reactive in that the damage has already been done, and otherwise lack the ability to prevent or undo the ill effects of the damage in the first place.

Current technology, as disclosed in U.S. Pat. Nos. 6,529,885, 6,811,082, 6,817,521, and 6,332,134, highlights a fundamental failing in the current state of the art. Such prior mechanisms require the identify owner to either use a "smart instrument," carry his own credit scanning device, or use a bank as a third party to a transaction as common as the simplest purchase. While these prior patents illustrate an attempt to address the issue of protecting and managing financial transactions, the solutions they present lack broader financial and non-financial application, practicability and/or simply substitute one flawed mechanism of protection and management for another. This is true in part because an identity owner has no means of proactively controlling use of his identity and identification information with a system designed specifically for such control.

SUMMARY OF THE INVENTION

Various embodiments of the invention improve security of identification information by giving an individual or other entity increased control over implied or direct use of his identity.

According to an embodiment of the invention, a method of protecting use of an entity's identity is provided. The method comprises setting a status of the identity to a first state, the first state defining a scope of permitted use of the identity, changing, in advance of an intended use of the identity, the status to a second state defining a scope of permitted use of the identity that is different front the first state, requesting use of the identity after the changing; and returning, after the requesting, the state back to the first state.

The above embodiment may have one or more preferable features, of which the following are non-limiting examples. The first state is a default state, and the returning occurs in response to completion of a use of the identity. The first state may comprise a default state, and the returning occurs in response to a predetermined number of uses of the identity, an elapse of a predetermined time after a predetermined event, or the earlier of the onset of the predetermined number of transactions and the predetermined time after the predetermined event. The predetermined event may comprise the changing, the requesting completion of a use of the identity which prompted the requesting, or dictated by a parameter within the second state. The use of the identity may comprise use of a credit card, debit card, check card, financial institution account number, brokerage account number, or other instrument provided by an account holder of record. The requesting may comprise transmitting, from a user of the identity to a service provider which maintains the state, a request for authorization to use the identity, where information in the request is insufficient to authorize the use of the identity.

According to another embodiment of the invention, a method of protecting use of an entity's identity is provided. The method comprises attempting to use an identity at a source, forwarding first information relating to the use to a user affiliated with the source location, forwarding second information from the user to a service provider, the second information being different from the first information, determining, by the service provider, whether the use of the identity is consistent with a pre-registered intent of the entity, and sending, from the service provider to the user, a decision based on the determining, wherein the second information is insufficient in and of itself to authorize any related use of the identity.

The above embodiment may have one or more preferable features, of which the following are non-limiting examples. The pre-registered intent of the user may comprise at least one of allowance of use, limitation of use, expansion of use, denial of use, or insufficient information to make a determination. The attempting to use may comprise entering information from a credit card or a debit card to facilitate a financial transaction, and the user is a company account holder of record of the credit card or debit card; making a request to access medical records of the entity, and the user is a healthcare related organization; making a request for a loan, and the user is a lender; or accessing a secure location, and the user is a security company.

According to yet another embodiment of the invention, a method of protecting use of an entity's identity is provided. The method comprises establishing, by the user, a set of desired identification information parameters, sending, from the user to a service provider, the set, obtaining, by the service provider from the entity, information from the entity consistent with the set, storing the information provided by the obtaining, and using, by the service provider, at least some of the information provided in the obtaining to respond to a request by the user to authorize a use of the identity of the entity, wherein the user does not have direct access to the information provided by the entity and subject to the storing.

The above embodiment may have one or more preferable features, of which the following are non-limiting examples. The set may comprise at least one of the entity's name, address, telephone number, personal identification number or biometric data. Preferably the user cannot authorize the use of the identity of the entity absent permission from the service provider. Preferably the service provider cannot provide the permission unless consistent with the intent of the entity as reflected in the results of the obtaining.

According to still yet another embodiment of the invention, there is provided a method of protecting use of an entity's identity. The method comprises storing, at a service provider, data representing first identification information of an entity, and at least one criteria capable of limiting the use of the identity, receiving, at a service provider, a request to determine whether the use of an entity's identity by a party is authorized for a requested application, the request including second identification information, comparing at least some of the first identification information with at least some of the second identification information, determining, based at least partially on a result of the comparing, whether the use of the identity by the identity-use-source is authorized for a particular application, and responding from the service provider to the identity-use-source consistent with the result of the determining.

The above embodiment may have one or more preferable features, of which the following are non-limiting examples. The responding further comprises sending a response, the response indicating one of allowance of use, denial of use, or insufficient information to make a determination. The method may further comprise receiving, from the entity, the data representing the first identification information and the identity use criteria. The receiving or responding may further comprise receiving or responding through a Web page, customer service representative, switched wired network, wireless network, in person, or any of combination thereof. The storing, determining, or responding may further comprise storing, determining, or responding by a service provider that is an electronic computing device. The storing, determining, or responding may further comprise storing, determining, or responding by an electronic computing device that further comprises hardware, software, or a combination of both hardware and software.

BRIEF DESCRIPTION OF THE DRAWINGS

The present invention is further described in the detailed description which follows, in reference to the noted plurality of drawings by way of non-limiting examples of certain embodiments of the present invention, in which like numerals represent like elements throughout the several views of the drawings, and wherein:

FIG. 6 depicts an example of an electronic interface that displays the identity owner's identification information and allowing for management of the identification information by the identity owner.

DETAILED DESCRIPTION OF THE EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
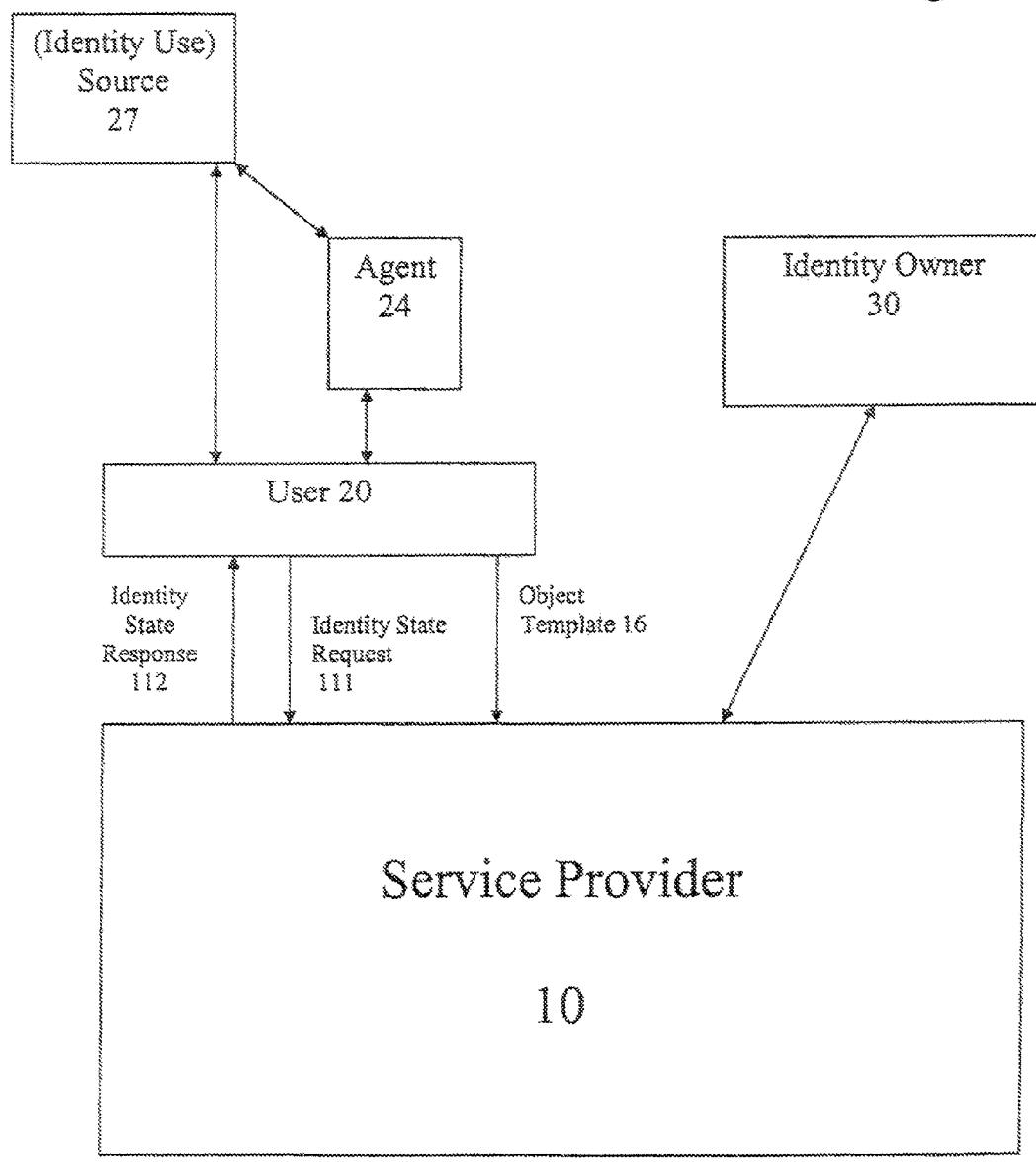
FIG. 1 is a diagram depicting at a high level the interconnections between elements of a system capable of implementing a particular embodiment of the invention.

Referring now to FIG. 1, the elements of a particular embodiment are illustrated where a service provider 10, a user 20 and an identity owner 30 interact to use an identity owner's identity and/or identification information. User 20 provides service provider 10 with an object template 16. Object template 16 contains various fields that define the type(s) and nature of information that service provider 10 preferably accepts and/or stores for any particular identity owner(s) 30. Identity owner 30 will in turn provide that information to service provider 10 for use in the authorization, limitation or denial of requests from user(s) 20 to use the identity of identity owner 30.

At some later point in time, an attempt will be made at a source 27 to use the identity of identity owner 30. The particulars of such use will be transmitted to user 20 either directly or indirectly through one or more agents 24. User 20 then sends an identity state request 111 to service provider 10, which requests authorization to complete the underlying transaction. Based on the information in identity state request 111 relative to information previously provided by identity owner 30, service provider 10 will determine whether to authorize, limit or deny the requested use. Service provider 10 sends an appropriate response to user 20 in an identity state response 112. User 20 in turn sends appropriate instructions to source 27 either directly or indirectly through one or more agents 24.

In the preferred embodiment, identity state request 111 preferably includes at least enough information to allow service provider 10 to locate the account information of the particular identity owner 30 and to determine the corresponding user instructions. However, the information in identity state request 111 is preferably in and of itself insufficient to enable the use of the identity for its intended use, such that its capture or loss would not expose vital information. By way of non-limiting example, if the triggering event is use of a credit card, then the credit card company (user 20) sends to service provider 10 in identity state request 111 the name, address and phone number of identity owner 30, as well as the last four digits of the credit card. From this information, service provider 10 can determine whether use of the credit card is authorized at that time. Yet the information in identity state request 111 is either public (name, address, and phone number being in phone books) and/or useless (four digits of a credit card being insufficient for a transaction). This provides a layer of protection to the use of the identity of an entity that is not confined to service provider 10.

Figure 2:
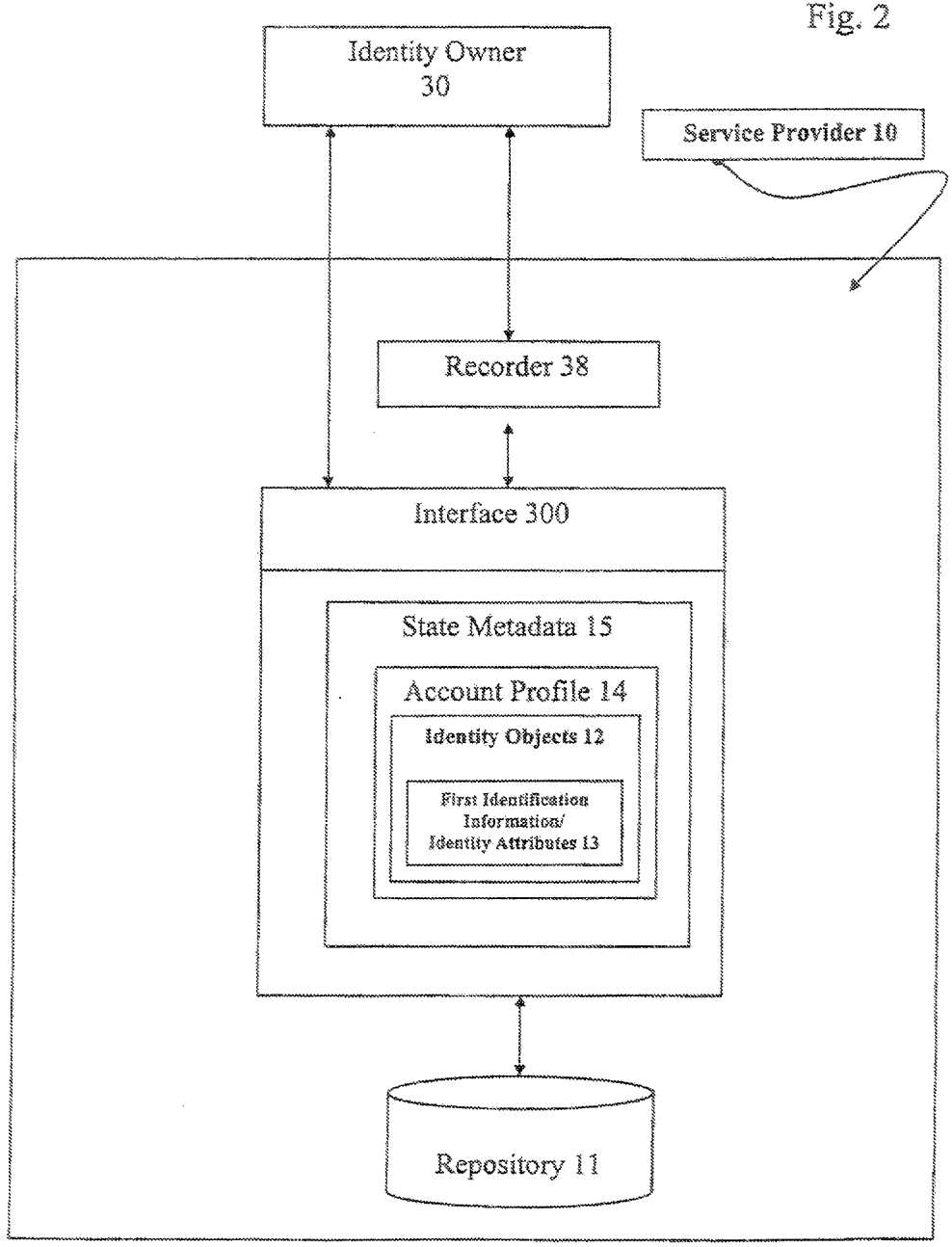
FIG. 2 is a diagram of a portion of an embodiment of the invention that depicts in more detail the interaction between, and around the identity owner and the service provider.

Referring now to FIG. 2, identity owner 30 interfaces with service provider 10, either directly or indirectly through a recorder 38 of service provider 10. Service provider 10 stores identification information and corresponding state metadata 15. (Metadata is understood in the electronic arts as data that is contained within an electronic file that is not necessarily needed to use the file, but rather contains information on the information within the file.) Identity state metadata 15 accompanies account profiles 14, with one or more of account profiles 14 being associated with a particular identity owner 30. Each account profile 14 preferably includes one or more identity objects 12. Each identity object 12 preferably includes one or more identity attributes 13. Identity attributes 13 represent identification information communicated to service provider 10 by identity owner 30 or an authorized surrogate of the identity owner 30. All of this information may be stored in a repository 11.

Service provider 10 is configured to allow identity owner 30 to set up, manage, and edit identification information stored in the corresponding account profile 14. Access to the account profile 14 is preferably at least password protected to prevent unauthorized access to the identification information.

The information which identity owner 30 provides to service provider 10 reflects the identity of the identity owner 30 to, by way of non-limiting example allow, deny, limit, secure, protect or otherwise control a type of use of the identity of an entity. The nature and scope of the control and management of identity use is essentially unlimited and based only on the parameters as may be defined by user 20 and identity owner 30. By way of non-limiting example, identity owner 30 could set up account profile 14 as follows:

(1) credit cards can only be used between 9 AM and 11 PM.

(2) medical information is available at all times but only to users 20 that are pre-authorized for health services (e.g., doctors, hospitals, pharmacies).

(3) applications for loans or new credit are never to be approved.

Limitations such as the above establish default and real-time use control over the identity of an identity owner 30. Attempts to use identity outside the authorized scope will be denied, preventing misuse before it takes place and identifying a possible fraud in progress for law enforcement response. If identity owner 30 needs to use its identity in a manner inconsistent with the above limitations, then identity owner 30 can modify account profile 14 in advance of such use and then return account profile 14 to its prior state (or any other desired state) after the need for the use concludes. It is also helpful for an identity owner 30 to be capable of modifying identification information on a whim, creating a real-time, or near real-time system that is fluid aid constantly capable of meeting the needs of identity owner 30 while securing the identification information.

Based on use limitations in account profile 14, service provider 10 will advise user 20 as to whether or not the transaction is approved or not in identity state response 112. Preferably, identity state response 112 is similar to identity state request 111 in that the information sent in identity state response 112 is sufficient to communicate the decision of service provider 10 but insufficient to enable the use of the identity for the intended use. Thus, capture or loss of identity state response 112 would not expose vital information. However, the contents of request 111 and response 112 may or may not overlap to varying degrees.

Figure 3:
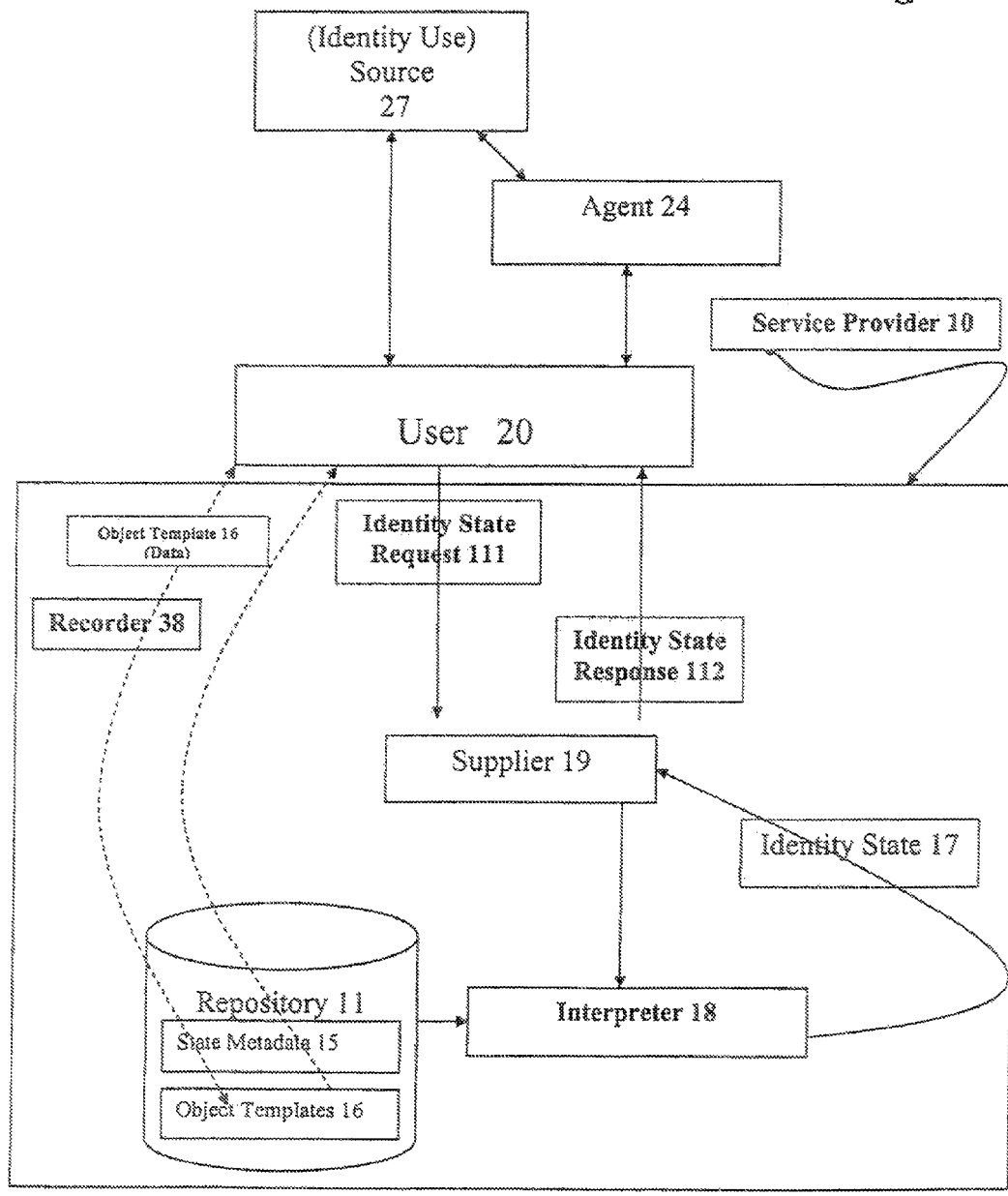
FIG. 3 is a diagram of a portion of an embodiment of the invention that depicts in more detail the interaction between and around the user and the service provider.

In certain circumstances, identify state response 112 may include actual identification information. Preferably, such a transfer would be limited to only those identification information attributes 13 that identity owner 30 has allowed for release to that particular user 20. In some cases identity state response 112 need only include the resulting identity state (e.g., "allow request" or "deny request"), without transmitting any other identification information of identity owner 30. The instruction to deny or allow a use under certain conditions is an example of an identity attribute 13. Such instructive identity attribute(s) 13 are referred to herein as the identity state 17 (shown in FIG. 3). In such situations, the connection between users 20 and service provider 10 (such as TCP, HTTP other land and/or wireless connections) may provide sufficient routing information to process identity state response 112 to its intended destination within user 20 without sending other specific identification information.

Thus, in the above example where service provider 10 decides to deny a request for use, identity state response 112 sent from service provider 10 to the user 20 includes content identity state 17, which represents the preexisting intent of identity owner 30 to deny the particular transaction. User 20 preferably complies with the identity state 17 and sends an appropriate denial message to source 27, either directly or through agent(s) 24.

The circumstances under which identity owner 30 elects to deny use of its identity are not limited to avoidance of fraud. Privacy and self-control considerations may also be a factor. For example, an identity owner 30 who wants to maintain confidentiality of his medical records, but wants to preserve quick access in emergencies can set identity attributes 13 in account profile 14 to only approve identity state requests 111 from authorized health-care-related institutions. In another example, an identity owner 30 who spends too much money at a certain store or type of store can set identity attributes 13 in account profile 14 to deny requests from that store or type of store.

Advantages of the preferred embodiment with respect to the contents of identity state request 111 and identity state response 112 will now be discussed. As discussed above, the substantive contents of these communications is preferably enough to determine and communicate the intent of identity owner 30 with respect to a particular use of identity. Particularly, identification information in identity state request 111 is insufficient in and of itself to facilitate the use intended by source 27, and identity state response 112 need include nothing more than identity state 17. As such, service provider 10 can perform its function of permitting, limiting or denying transactions without receiving, storing, or sending identification information that enables the underlying use ("use-enabling information").

Thus, service provider 10 authorizes or denies requests without having access to sensitive identification information, such as, by way of nom-limiting example, a full credit card number or Personal Identification Number (PIN). Service provider 10 thus does not have enough information to take any action on its own. For example, service provider 10 would not be able to misuse the credit card of identify owner 30 because it would not have the credit card or the credit number. Thus, while service provider 10 authorizes transactions, it cannot by acting alone misuse the underlying instruments that trigger the transactions. In theory, service provider 10 may nonetheless have access to some of this information, although such information can be protected using passwords, encryption, or other known techniques.

Similarly, user 20 will preferably know whether to authorize or deny a transaction without receiving any new identification information from service provider 10 other than identity state 17. Since user 20 does not have direct access to other information in account profile 14, user 20 does not have information that could enable other undesired uses. By way of non-limiting example, if user 20 is a credit card company, it would not have enough information to access the medical records of identity owner 30. Without possession of use-enabling information, service provider 10 obviously cannot or cause user 20 to divulge information to agent(s) 24 and/or source 27. The identity owner's identification information account profile 14 therefore need never pass beyond the protection of the service provider 10.

The service provider 10 may also be tasked with securing identification information so as to prevent unauthorized access to the identification information. In a preferred embodiment, the security of identification information afforded by the service provider 10 is far reaching, dynamic and may contain one or more layers. As a threshold issue, the service provider 10 would preferably take the barest, directly identifying, raw data of an identity owner 30, if any, encrypt it and secure it preferably never to be used again.

In another embodiment, service provider 10 acts as a centralized location relative to multiple users 20 for the storage of identification information of identity owners 30. That is, rather than disseminating identification information to every bank, credit agency, insurance company, or any other entity that requests identification information, an identity owner 30 would disclose identification information to the service provider 10 instead. In this embodiment, these various users 20 would make identity state requests 111 to the service provider 10, which would determine what, if any, identification information is disclosed to users 20. An embodiment such as this that includes service provider 10 can, at a minimum, reduce the number of institutions privy to sensitive identification information.

Service provider 10 preferably is a company that includes employees that operate the necessary computer hardware and software to secure identification information and to communicate with identity owners 30 and users 20. In an alternative embodiment, service provider 10 is an automated combination of hardware and software that carries out the operations described herein. By way of non-limiting example, an identity owner 30 can utilize either a computer service provider 10 that is maintained by an outside party or a computer maintained by the identity owner 30 to prevent unauthorized access to identification information (e.g., a human identity owner 30 may, for the purpose of practicing this embodiment, maintain and/or utilize a personal computer as a service provider 10). In this example, the service provider 10 is a computer, preferably a server, accessible to the identity owner 30 and the user 20 through a communication network that is maintained by the computer. The computer in this example would preferably be programmed to provide responses to user 20 based on input from the user 20 and the identity owner 30.

Identity owner 30 is preferably an individual, a corporation, or a computer system. Preferably, the identity owner 30 will contact service provider 10 and request that the service provider 10 secure the identity owner's identification information subject to provided constraints. Service provider 10 might, for example, employ a layered technique where the identify owner's raw identification information, such as social security number or other primary identification data, biometric data, address, phone number(s), and other such information, is encrypted in a separately secure layer. With raw identification information secure in a fundamental layer, the service provider 10 can then use an additional layer of security for protecting the encrypted identification information from misuse.

User 20 may be thought of as a credit lender who wants to access the records of repository 11. User 20 may be, by way of non-limiting example, a credit card company, credit reporting agency, merchant, banking institution, brokerage firm, insurance provider, hospital, medical caregiver, computer, corporation, or family member. User 20 may also in theory be an imposter. In the preferred embodiment, the service provider 10 will implement double-checks and safeguards so as to help protect the identification information from imposters.

User 20 sends identity state requests 111 in response to a triggering event at identity use source 27. Identity use source 27 sends desired transaction-based information, which preferably would include the identity of source 27 and the amount of fee transaction (if a financial-based transaction). Service provider 10 can then respond to user 20 with information or instructions that will determine the next step in the transaction precipitated by the triggering identity use source 27. In the preferred embodiment, the instructions received by user 20 will properly control the transaction and provide the result desired by identity owner 30 and user 20.

A non-limiting example of an end-to-end exchange is as follows. For set up, user 20, which in this example is a credit card company, will have previously given service provider 10 an object template 16. Object template 16 defines the identification information that user 20 needs in order to process a transaction by source 27. Identity owner 30 provides service provider 10 with the corresponding identification information through interface 300, such as a Web page.

At a later point in time, a credit card is offered to complete a transaction at source 27. Source 27 communicates the details of the transaction, as well as any desired details, to user 20. User 20 forms an appropriate identity state request 111 and sends it to service provider 10. Service provider 10 compares the contents of the identity state request with the identity object(s) 12 which describe the intent of identity owner 30 with regard to the particular transaction. Service provider 10 determines whether the transaction is authorized or not, and then sends a corresponding identity state response 112 to user 20. In addition, service provider 10 may release other identification information to user 20 as may be authorized by the identity object(s) 12 within account profile 14.

In a related example, object template 16 allows an identity owner 30 to set the default status of the credit identification instrument (e.g., the credit card or underlying account) as on or off. In this example, identity owner 30 sets the default of the credit card to "deny," essentially placing the use of the credit card, in a lockdown state. If identity owner 30 wants to use the credit card at a particular time, then identity owner 30 can contact service provider 10 via, e.g., the Internet to change identity state 17 at the appropriate time, such as between 12:30 PM and 2:30 PM that day. Identity owner 30 makes the purchase, or not, secure in the knowledge that use of the credit instrument was permitted within that limited two-hour window. Before the window opens, and after it closes, the default state is "deny," thus preventing any unauthorized (or even authorized) use outside that window.

User 20 sends identity state request 111 in response to a use of identity at source 27. By way of non-limiting example, source 27 can be initiated by a person, a credit instrument, an Internet transmission, the identity owner 30, an imposter, user 20, or agent 24. In a credit card example, source 27 may be the point-of-sale terminal through which the credit card is scanned.

In a preferred embodiment, user 20 is a lending institution such as a bank, identity owner 30 is a person, and service provider 10 is a form of company that preferably would use, by way of non-limiting example, electronic methodology such as a computer server to provide a network through which all parties to the transaction can communicate. By way of non-limiting example, the service provider 10 could be a corporation or company whose sole purpose is directed to management of identification information; the service provider 10 could just as well be a credit reporting agency, insurance agency, health agency, or any established entity that has been enabled to practice the invention. Also, by way of non-limiting example, the network may take the form of voice communication (e.g., through telephony or by face-to-face encounter) or an electronic interconnection such as an Internet or intranet Web browser interface, or any wireless or direct interface assisted by a software component such as a client-side application.

In an embodiment, the process may begin when the service provider 10 sets up an object template 16 (e.g., a template that defines the options for an identity owner 30 to establish an account profile 14 to contain its identification information). The process may also begin when a user 20 (e.g., a credit provider) contacts the service provider 10 and sets up an object template 16 (e.g., criteria an identity owner 30 must disclose for a particular transaction, or set of transactions, with that particular user 20 type). Identity owner 30 (Joe E. Patent) establishes an account profile 14 with a service provider 10. For simplicity, assume that at the end of the process, the following information exists in the database, or repository 11, of service provider 10. For example:

Account profile 14 data
Account ID: CACTUS
Account password: flowersforalgernon
Name: Joe E. Patent
Address: 102 Brown Street
Primary identification number: 222-22-2222

Next, the identity owner 30 protects a credit instrument event. For example, suppose XYZ Corporation provides object template 16 that requires six information fields. Five of the fields are required to "query" the identity state 17 of the identity object 12 (if any), and one field contains the identity state 17 of the identity object 12 last set by the identity owner 30. For example:

Identity object 12 data
Identity object type: XYZPer
Identity object account suffix: 565787
Identity object account name: Joe E. Patent
Identify object account phone: (555) 716-5555
Identity object account zip: 55555
Identity object state: permit In the above example, the five data fields can replace the need for use-enabling information, such as, for example, the credit instrument number. However, the information in these fields alone is insufficient to enable the desired use of the identify of identify owner 30, such that service provider 10 cannot misuse the identity. The sixth field, "permit", is necessary to illustrate the role of the service provider 10 as a gatekeeper so that an attempted use of the identity of identity owner 30 must pass before user 20 can follow through on the intended use.

Figure 5:
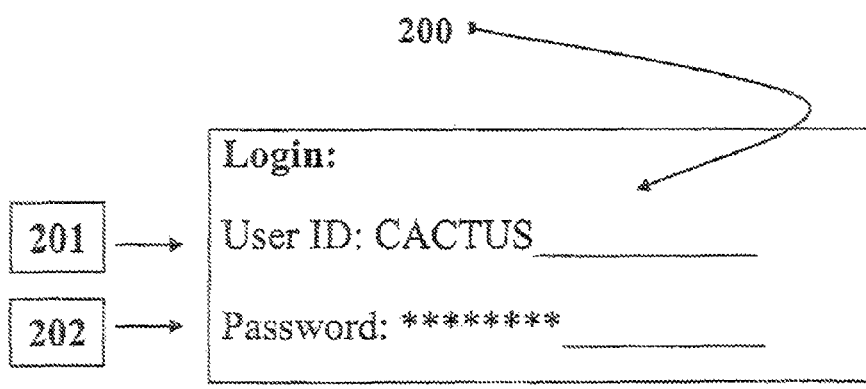
FIG. 5 depicts an example of a layer of security embodied by an electronic interface allowing an identity owner access to their identification information.

If, for example, a credit instrument of identity owner 30 is misplaced, then it is a simple matter for the identity owner 30 to contact the service provider 10 and change identity state 17 of the XYZPer identity object 12 to "deny" until certain that the instrument is not lost. By way of non-limiting example, this can be accomplished by the identity owner 30 accessing interface 300 and making the necessary changes. That layer of security, in addition to the preferred implementation of an outer shell of interface security 200, as shown in FIG. 5, and other possible layers of security such as, by way of non-limiting example, encryption methods of identification information, is a preferred benefit to the embodiment.

Continuing the example, a thief attempts to use the XYZ instrument at a merchant agent 24. This is an attempted use of identity at source 27, a transaction that implies or directly uses identification information. The merchant communicates the transaction information to user 20, in this case the XYZ transaction approval network. XYZ generates an appropriate identity state request 111 and sends it to service provider 10. An example of the contents of the corresponding identity state request 111 is as follows:

<Identity request>
<Identity object type>XYZPer<Identity object type/>
<Identity object account suffix>565787<Identity object account suffix/>
<Identity object account name>Joe E. Patent<Identity object account name/>
<Identity object account phone>5555555555<Identity object account phone/>
<Identity object account zip>55555<Identity object account zip/>
<Identity request/>

In this example, with the exception of the primary identification data, nothing exists in the account profile 14 that has any security implication. Note that the primary identification data need not be alphanumeric. There may exist embodiments where it is preferable to include primary identification data that is biometric (fingerprint or retinal image). Once the primary identification data is entered at the time the account profile 14 is created (and indeed, if the data is numeric, it may not be necessary to store the full primary identification number in an implementation of the embodiment), this information is preferably encrypted.

Preferably, the responsibility of sending identity state request 111 to service provider 10 is allocated to the holder of record for account information related directly to the identity use by source 27. Typically this will be user 20 (XYZ in this example) or a representative of user 20. Either way, there must be sufficient information to supply data conforming to the identity object template 16 requirements and to positively match the identity objects 12 associated with the identity account profile 14.

An account profile 14 is accessible to the identity owner 30 either directly with service provider 10 or indirectly though recorder 38. Through access to the account profile 14, the identity owner 30 is able to observe, add, delete, and modify its state identity information. Multiple identity objects 12 and/or account profiles 14 may exist for each identity owner 30.

User 20 establishes the types of identification information to be used in object template 16, but preferably does not have access to account profile(s) 14 that contain the information itself. Object templates 16 can streamline a transaction by providing advance notice to an identity owner 30 of the specific identification information required by the user 20. Furnishing an identity owner 30 with an object template 16 is preferably accomplished either through one of the recorders 38 of the service provider 10 or by direct input of the object template 16 into the repository 11.

Figure 4:
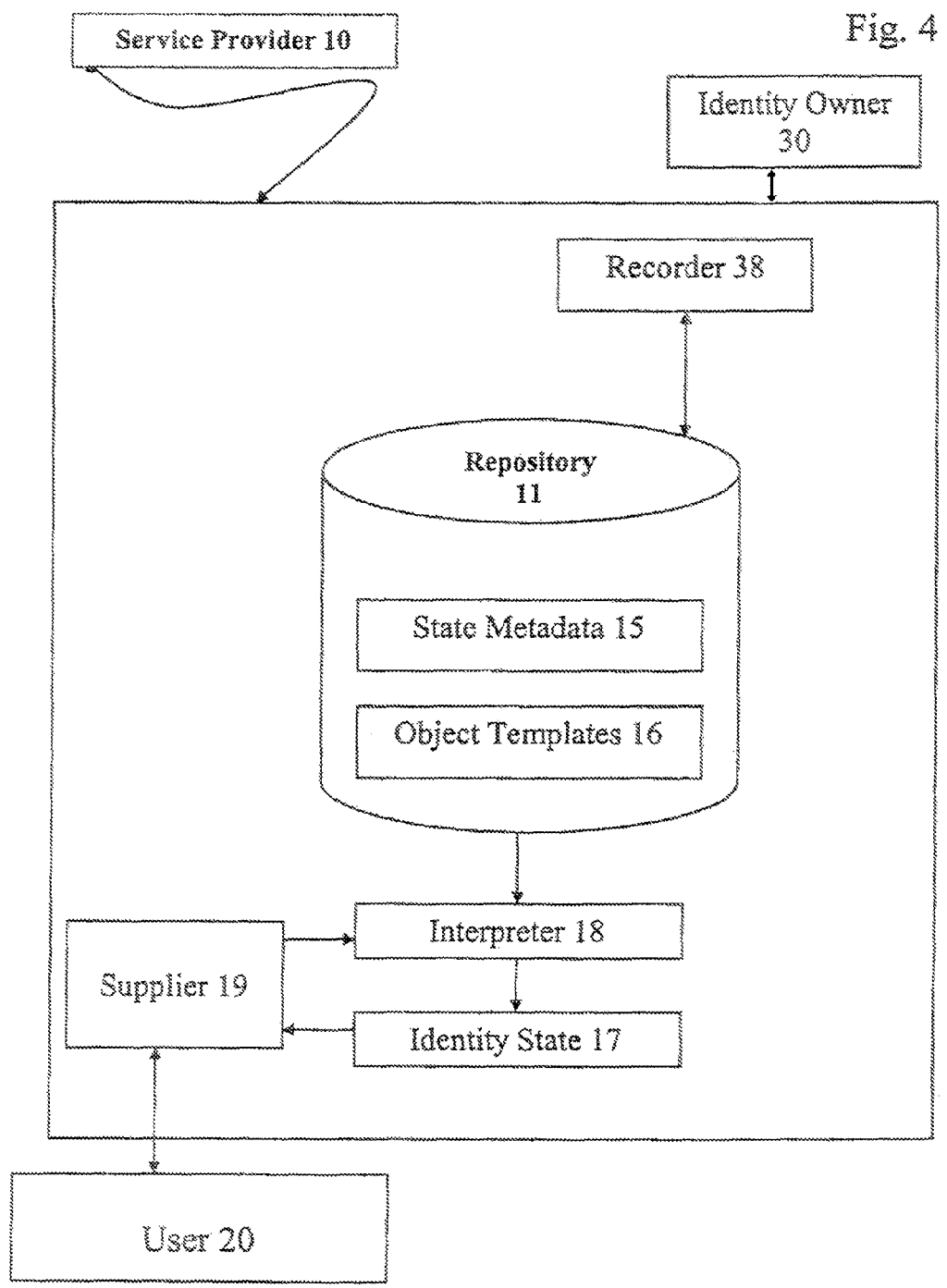
FIG. 4 is a diagram depicting the service provider in more detail as well as depicting the interconnections between elements of a system capable of implementing a particular embodiment of the invention.

Referring now to FIG. 4, an embodiment of service provider 10 is illustrated in detail. Object templates 16, akin to those described above, allow user 20 to practice proactively. To an extent, the types of identity objects 12 available to identity owner 30 are controlled by user 20 through the creation of object templates 16. Object templates 16 provide the criteria for identity state request 111, identity response 112, and attribution of identity objects 12. Stated another way, in certain dealings the identity owner 30 can only create personalized identity objects 12 for which users 20 have created object templates 16. The reason for this is that having the resources available to protect identity are ineffective unless user 20 (those relying on identity to act on behalf of identity owner 30) are prepared to cooperate with service provider 10. Preferably, object templates 16 provide user 20 with sufficient control and efficiency that will encourage the cooperation of user 20.

Identity state 17 is the result of the comparison between identity state request 111 and identity objects 12 input by identity owner 30. Whenever possible, it is preferable for service provider 10 to provide identify state 17 while avoiding disclosure of extra identification information of an identity owner 30. In a preferred embodiment of the invention, the service provider 10 accomplishes this through use of an interpreter 18. On instruction from, for example, user 20, recorder 38, identity owner 30, or a supplier 19 of service provider 10, interpreter 18 will compare the identity state request 111 and at least one identity object 12 for a particular identity owner 30. Preferably, interpreter 18 can also compare identity state requests 111 that are formulated based on requirements described by applicable object templates 16, as well as against criteria set by the identity owner 30.

By way of non-limiting example, if a merchant user 20 issues an identity state request 111 for a purchase at 3:00 AM and the corresponding identity owner 30 has not authorized such transactions at that hour, then interpreter 18 transmits the identity state response 112 by informing the user 20, either directly or indirectly through supplier 19, that the purchase is "denied." Identity state 17 may be based on one or more identity objects 12; in this case, the identity object 12 must have contained identity attributes 13 such as "at 3:00 AM", "off" or a time period that includes 3:00 AM, designated as "off" (e.g., 2:00 AM-4:00 AM).

Interpreter 18 thus evaluates identity state request 111 against the criteria, rules and requirements contained in the state identity object 12 of the identity owner. After evaluation, interpreter 18 preferably communicates the result of the analysis, either directly or indirectly, to user 20 without disclosing sensitive identification information. Instead, the identity state response 112 only contains the stares of a transaction (in this example, the status is the "identity state" 17) involving identification information. Interpreter 18 and supplier 19 are preferably the entities within service provider 10 with access to state metadata 15. Interpreter 18 and supplier 19 may be people and/or electronic devices such as computers that implement algorithms designed to assess and interpret an identity state 17 as described herein. Non-limiting examples of potential identity state 17 responses 112 include: permit, deny, not enough information, and permit only for emergency use. By way of non-limiting example, the latter response would exist in a preferred embodiment that included identification information that was medical in nature. An identity owner 30 may authorize release of his medical history to known licensed caregivers only in the case of an emergency.

By way of further example, there may be a second object template 16 that defines the requirements for controlling identity relative to acquiring additional credit. In this example, a customer applies for a loan at a federal bank. Here, the customer triggers identity use source 27 (the bank) that initiates the steps described herein. As part of the loan application, the customer represents on the loan application that his primary identification data value is 555-55-5555. As a matter of course, the Federal Bank would contact a credit reporting agency to obtain a credit worthiness report for the loan applicant. The credit reporting agency (a user 20) would determine if the loan applicant had an identity account profile 14. The service provider 10 would have reported the fact that identity owner 30 had such an account in the normal course of business. After discovering the presence of an identity account profile 14 in the credit information of the loan applicant, the credit reporting agency contacts supplier 19 and requests identity state 17, based on its "new credit" object template 16, for a customer having a primary identification data value of 555-55-5555. Interpreter 18, acting as an agent of service provider 10 as opposed to the credit reporting agency as user 20, determines identity state 17. Once found, the "new credit" object template 16 is compared to the corresponding identity object(s) 12. The interpreter 18 ensures that all fields match.

After noting the account profile number associated with the customer name provided by the bank (Account No. CACTUS), interpreter 18 accesses and confirms that the primary identification data value matches the one in the original identity state request 111. Further examination of identity objects 12 in account profile 14 shows that identity state 17 has been set to "Type—Identity Off". Since no other identity objects 12 exist for this identity owner 30 that supersede this identity state 17, interpreter 18 informs supplier 19 that identity state 17 is "deny" and, thus, any use of the identification information of identity owner 30 should be denied. Supplier sends this identity state 17 to the credit reporting agency in the manner discussed herein. The credit reporting agency communicates this state to the Federal Bank that requested the loan applicant credit report.

At this point the federal bank knows that one of two situations exists. Either the person applying for the loan forgot to change their identity object 12 before applying for the loan, or the person making the application is trying to fraudulently obtain a loan. If the person is the legitimate identity owner, then the error can be corrected. If the person is an impostor, the fraud is revealed.

Using state metadata 15, it is possible to determine the identity attribute information 13 of identity owner 30. The state metadata 15 represents identity attribute information 13 of identity owner 30. State metadata 15 alteration by identity owner 30 permits control over the state metadata 15 and, thus, bestows an identity owner 30 with control over the use of its identity and identification information.

As seen in FIGS. 5 and 6, discussed in detail below, identity attributes 13 may be entered directly by identity owners 30 acting on their own behalf as identity recorders 38. This process may be achieved in person, by phone, wireless device, Web browser or any other device capable of communicating instructions of identity owner 30.

In another example, identity owner 30 decides to use a credit instrument for a vacation outside the United States, but notes that his account profile 14 prevents use of his identification information outside the United States ("USA Only"). Identity owner 30 accordingly decides to modify his account profile 14 through a call to recorder 38. Recorder 38 will go through one or more security protocols, such as a password check, date of birth, the last four characters of a primary identification data value, etc. The recorder 38 is satisfied that the caller is identity owner 30 of identity account profile 14 CACTUS. Identity owner 30 communicates his intent for use of XYZ credit instrument's transactions to be enabled outside the United States. Identity owner 30 is then asked to supply the last six digits of the account number and the phone number including the area code associated with this credit instrument account.

Service provider 10, preferably by using an authorized interpreter 18, examines the existing identity objects 12 to make sure that none of the identity objects 12 already refers to this credit instrument. If no entries exist, recorder 38 inputs an identity object 12 into the repository 11, "Type—Credit Usage—permit globally, instrument type XYZ Corporation, account suffix 565787, phone 5555555555". This allows usage of the instrument xxxxxx565787 outside the United States. As illustrated in the above example, an identity owner 30 may record identity attributes 13 and transmit these by mail, courier, electronic transmission or voice to recorder(s) 38 acting on the behalf of identity owner 30.

Storage, transmission, and disclosure of identity objects 12 are configured to resist compromise of the security of the identification information of the identity owner 30. The fact that identity attributes 13 are a partial representation of the identity object 12 is significant because it prevents the state metadata 15 from containing information that could jeopardize security of the identity owner 30 if breached.

Referring to FIG. 5 an identity owner 30 communicates through a security layer 200 that hinders unauthorized access to the identification information of identity owner 30. In this embodiment, service provider 10 has a software barrier in the form of a log-in screen interface which requires a username 201 and a password 202. Referring to FIG. 6, an identity owner 30 practicing the preferred embodiment can, after successful authorization, access its account profile 14. Preferably the accessed data appears in a convenient layout, preferably all in one view.

An example of interface 300 is depicted in FIG. 6 as one of many methods of layout for viewing, deleting, adding, and manipulating account profile 14. Interface 300 is essentially split into four topical sections. The topmost section contains an identity object 12 manipulation workspace 303. Workspace 303 is the area where identity owner 30 and recorder 38 can access and modify identity objects 12. Though not granted direct access, it is preferable that user 20 is granted the ability to use supplier 19 to deposit an object template 16 into repository 11 for use by identity owner 30 and/or recorder 38. It is also possible to give user 20 a more direct, write-only type of access to the repository 11. In the case of the example illustrated by FIG. 6, identity owner 30 would only be able to configure an identity object 12 for an XYZ credit instrument if XYZ company had previously provided an object template 16 for this type of financial instrument.

The second area of workspace 303 is the control set 309. Control set 309 is where either identity owner 30 or recorder 38 (at the behest of the identity owner 30) can manipulate identity objects 12. By way of non-limiting example, the identity attribute 13 "Parking Space 3R" can be set to "deny Crystal McCity access to location information." By way of further non-limiting example, this portion of workspace 303 is where identity objects 12 and identity attributes 13, such as "1 transaction per day", can be added to, for example, identity attribute 13 "bank account withdrawals" to form an identity object 12 that places a limit on the number of transactions for a particular bank account per day.

The bottommost two sections 320, 330 consist of one section that has two distinct portions, and it may have a name such as Recent Activity Monitor or Transaction Notification 330. In this section, it is possible for identity owner 30 or interpreter 18 (at the behest of identity owner 30), to monitor use of various identity-related activities such as credit instrument usage, or, as seen in FIG. 6, passport usage 330. After entering the appropriate data 390 in the Name Set Add/Modify field 320, the data is used to create an identity object 12 representing a name and address related to the account profile 14. The name of this set can act as a short form reference to a particular name and address and help the user avoid the re-entry of name and address data for identity assets sharing common attributes. Field 330 is illustrative of how the identity owner 30 and/or the authorities have a tool with which to track usage of such things as passports, credit instruments, ID tags, or even keys/key instruments to buildings.

Another embodiment of the invention applies to brokerage firms and investors. Identity owner 30 is again an entity, human or otherwise, capable of making investments in securities. User 20 is a brokerage firm. Service provider 10 maintains its function as an entity that can, but need not, encrypt and store the most fundamental and sensitive data in a separately secure layer. Similar to the steps disclosed above, this embodiment affords preventative security against misuse of any investment account.

Although the above-mentioned embodiments have been predominantly described in terms of financial transactions, the invention is not so limited. For example, FIG. 6 depicts how certain embodiments can be used to determine the details surrounding the identification information use for a passport. Each occurrence of the passport usage is listed. A transaction notification 330 is optional but can be a useful tool allowing the identity owner 30 to monitor the use of identification information. Indeed, it implicates, essentially, other embodiments that can be used in law enforcement.

Another non-financial use is monitoring of an identifying building access key, key instrument, or any locating device and is not limited to building area entry and exit monitoring. Such use would allow the system to track the location of the occupants of a building based on where they last used their key. This could be life saving in an emergency or, on the other hand, help the security or management of a building discern likely suspects after discovery of an unscrupulous act.

Another non-financial use is the protection of data that is medical in nature. Food allergies and diseases such as diabetes are non-limiting examples of such medical information that an identity owner 30 would not want accessed by anyone other than, for example, a licensed medical professional or licensed medical professional organization. Such systems provide, on a consistent, easily transferable basis, information as might be required as part of standard service industry entity (e.g., dentists, physicians, veterinarians, schools) registration procedures, such information and name, address, and contact information.

In a law enforcement embodiment, identity owner 30 is operating with the cooperation of or under the control of law enforcement. In this embodiment, certain "zones" may be set up relative to the person's identity. For example, a sex offender may not be able to leave the local jurisdiction, or someone under house arrest cannot leave the home. Flags can be set up in object template 16 or related operations that monitor use of identity and alert law enforcement if the use is for a prescribed activity or in a prescribed area.

It is noted that the foregoing examples have been provided merely for the purpose of explanation and are in no way to be construed as limiting of the present invention. While the present invention has been described with reference to certain embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method for a service provider to control use of an entity's financial account to facilitate transactions, comprising:
   setting scope of use, defined by the entity via a network, for the financial account, including at least:
   (a) the financial account to either OFF or ON;
   (b) for a plurality of individual categories, whether each category is authorized or unauthorized for transactions using the financial account, each category representing a different type of transaction partner; and
   (c) a geographical scope reflecting a geographic area in which transactions are authorized;
   receiving, via a network from a source other than the entity, an inquiry regarding a proposed transaction that would use the financial account;
   determining, relative to the scope of use, whether the financial account may or may not be used for the proposed transaction, comprising:
   denying when the financial account is OFF;
   denying when the financial account is ON and the proposed transaction falls within a category that is unauthorized;
   denying when the financial account is ON, the proposed transaction falls within a category that is authorized and when a location of the proposed transaction is outside of the geographical area;
   permitting when (a) the financial account is ON, (b) the proposed transaction falls within a category that is authorized, (c) a location of the proposed transaction is inside the geographical area, and (d) the proposed transaction is not otherwise impermissible; and
   responding to the inquiry by providing, via a network to the source, first information based on the result of the determining.

2. The method of claim 1, wherein content of the inquiry is insufficient to allow the service provider to execute the proposed transaction, such that the service provider could not use the contents of the inquiry alone to fraudulently execute other transactions.

3. The method of claim 1, wherein the entity's financial account has an assigned code, the method further comprising:
   the receiving the inquiry comprises receiving only a portion of the assigned code;
   wherein the entire assigned code is needed to execute the proposed transaction, such that the service provider's possession of only the portion of the assigned code is alone insufficient to allow the service provider to fraudulently execute other transactions.

4. The method of claim 1 wherein the setting for the plurality of individual categories further comprises setting at least one category to authorized, and setting at least one other category to unauthorized.

5. The method of claim 1, wherein the financial account is a credit card account or debit card account.

6. The method of claim 1, further comprising:
   receiving second information representing the entity's desired scope of use of the financial account;
   wherein the scope of use is defined by the received second information.

7. A method for a service provider to control use of an entity's financial account to facilitate transactions, the method being executed on electronic computer hardware in combination with software, the method comprising:
   setting scope of use, as defined by the entity via a network, for the financial account, including at least:
   (a) setting a state status of the financial account to either an OFF or ON state;
   (b) setting a category status for each category of a plurality of categories as either authorized or unauthorized for transactions using the financial account, each category representing a type of transaction partner; and
   (c) setting a distance from the entity, where the entity's financial account can be used within said distance;
   receiving, via a network from a source other than the entity, an inquiry regarding a proposed transaction on the financial account;
   determining, relative to the scope of use, a response status to the inquiry reflecting whether the financial account may or may not be used for the proposed transaction, comprising:
   setting the response status to impermissible when the state status for the financial account is OFF;
   setting the response status to impermissible when the state status for the financial account is ON and the proposed transaction falls within a category having an unauthorized category status;
   setting the response status to impermissible when the state status for the financial account is ON, the proposed transaction falls within a category having an authorized category status and the distance from the entity where the entity's financial account can be used is outside said distance;
   setting the response status to permissible when (a) the state status of the financial account is ON, (b) the proposed transaction falls within a category having an authorized category status, (c) the distance from the entity where the entity's financial account can be used is within said distance, and (d) the proposed transaction is not otherwise impermissible; and
   responding to the inquiry by providing, via a network to the source, first information based on the response status of the determining.

8. The method of claim 7, wherein the contents of the inquiry is insufficient to allow the service provider to execute the proposed transaction, such that the service provider could not use the contents of the inquiry alone to fraudulently execute other transactions.

9. The method of claim 7 wherein the setting the category status further comprises setting at least one category to authorized status, and setting at least other one category to unauthorized status.

10. The method of claim 7, wherein the financial account is a credit card account or debit card account.

11. The method of claim 7, wherein the scope of use further comprise a geographic scope reflecting a geographic area in which transactions are authorized, and the determining further comprises setting the response status to impermissible when a location of the proposed transaction is outside of the geographic area.

12. The method of claim 7, further comprising:
receiving second information representing the entity's desired scope of use of the financial account, and
wherein the scope of use is defined by the received second information.

13. A method of protecting use of an entity's financial account, the method being executed on electronic computer hardware in combination with software, the method comprising:
storing data representing:
first identification information of an entity; and
at least one criteria previously defined by the entity for allowing and/or limiting the use of the financial account, the at least one criteria defining at least one non-monetary circumstance under which the financial account can be used;
receiving, via a network from a source other than the entity, a request to determine whether a proposed use of the entity's financial account by a party at a location is allowable, the request including second identification information;
comparing at least some of the first identification information with at least some of the second identification information;
determining whether the proposed use of the entity's financial account by the party at the location is authorized for the proposed use, comprising:
determining whether the entity's financial account is in an entity established ON or OFF state;
determining whether or not the at least one criteria blocks the proposed use, with the at least one criteria blocks comprising at least one of:
a geographical limitation on where the financial account can be used; and
a distance from the entity within which the financial account can be used; and
responding to the request by providing, via a network to the source, response information based on the result of said determining.

14. The method of claim 1, wherein:
the setting scope of use further includes (c) setting geographic limitations on where the financial account can be used; and
wherein a proposed transaction that originates outside of the geographic limitations is considered impermissible for the determining.

15. The method of claim 7, wherein:
the setting scope of use further includes (c) setting geographic limitations on where the financial account can be used; and
wherein a proposed transaction that originates outside of the geographic limitations is considered impermissible for the determining.

16. The method of claim 1, wherein:
the setting scope of use further includes (c) setting a distance from the entity, where the entity's financial account can be used within said distance; and
wherein a proposed transaction that originates from beyond the distance is considered impermissible for the determining.

* * * * *